(12) United States Patent
Boyer et al.

(10) Patent No.: US 9,131,974 B1
(45) Date of Patent: Sep. 15, 2015

(54) DEVICE FOR FACILITATING ARTIFICIAL PROSTHESIS INSTALLATION WITH MEASURED APPLIED PRESSURE AND METHOD THEREFOR

(71) Applicant: Joint Solutions, Inc., Henrico, VA (US)

(72) Inventors: John Stuart Boyer, Henrico, VA (US); Bruce Reed Anderson, Richmond, VA (US)

(73) Assignee: Boyer Anderson, LLC, Henrico, VA (US)

( * ) Notice: Subject to any disclaimer, the term of this patent is extended or adjusted under 35 U.S.C. 154(b) by 0 days.

(21) Appl. No.: 14/575,160

(22) Filed: Dec. 18, 2014

Related U.S. Application Data

(60) Provisional application No. 62/031,946, filed on Aug. 1, 2014, provisional application No. 61/985,175, filed on Apr. 28, 2014.

(51) Int. Cl.
*A61B 17/88* (2006.01)
*A61B 17/17* (2006.01)
*B25B 5/10* (2006.01)

(52) U.S. Cl.
CPC ......... *A61B 17/8802* (2013.01); *A61B 17/1767* (2013.01); *B25B 5/10* (2013.01)

(58) Field of Classification Search
CPC .............................. A61B 17/1767; B25B 5/10
See application file for complete search history.

(56) References Cited

U.S. PATENT DOCUMENTS

2013/0190604 A1* 7/2013 Moffatt .................. 600/411

OTHER PUBLICATIONS

International Search Report and Written Opinion for PCT/US15/27723, USPTO, May 22, 2015.

* cited by examiner

*Primary Examiner* — Andrew Yang
(74) *Attorney, Agent, or Firm* — Williams Mullen, PC; Thomas F. Bergert

(57) ABSTRACT

Devices and methods provide for measuring applied pressure on an article, such as a patella construct during a surgical procedure. Embodiments include a clamp having an upper frame arm, a lower frame arm and a clamp assembly, and further include a clamp with a knob assembly and a pressure monitor assembly. Differently sized clamp inserts can be interchangeably employed with a clamp stem to adapt to the relative sizes of objects being clamped.

28 Claims, 12 Drawing Sheets

FIG. 9
FIG. 10
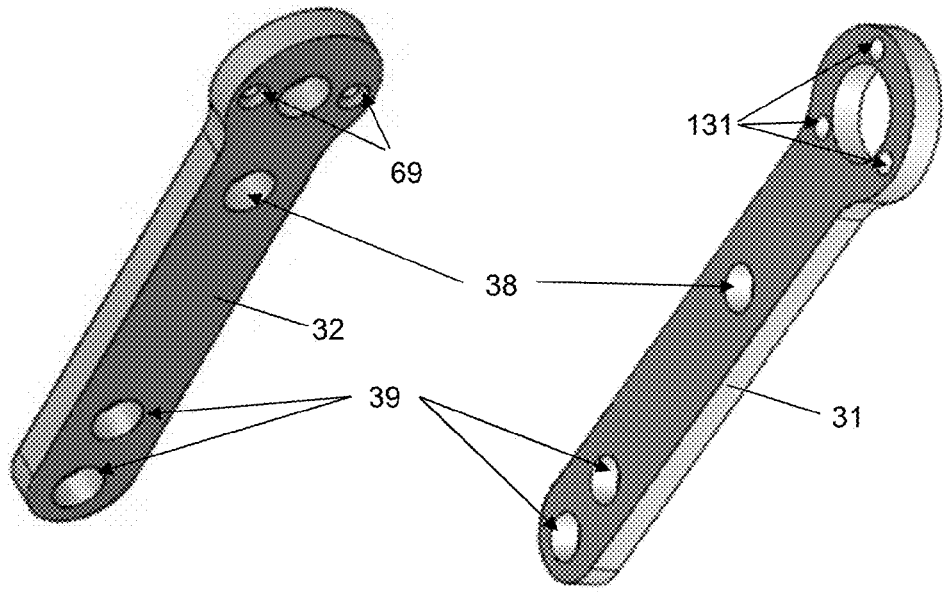
FIG. 11
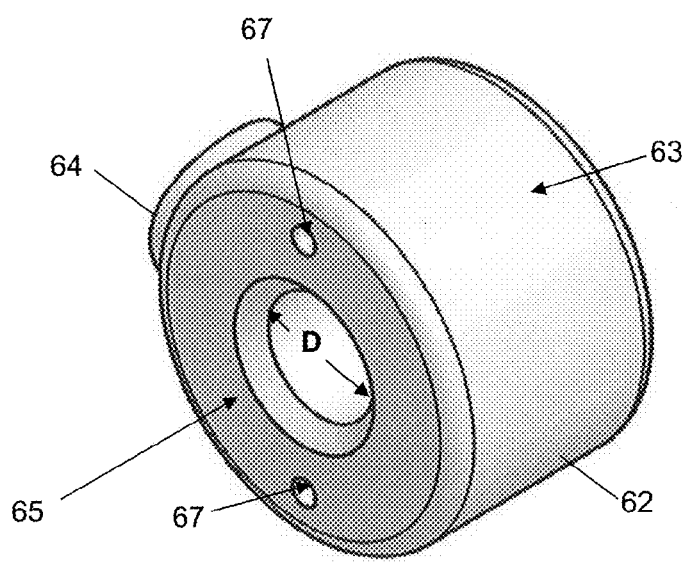

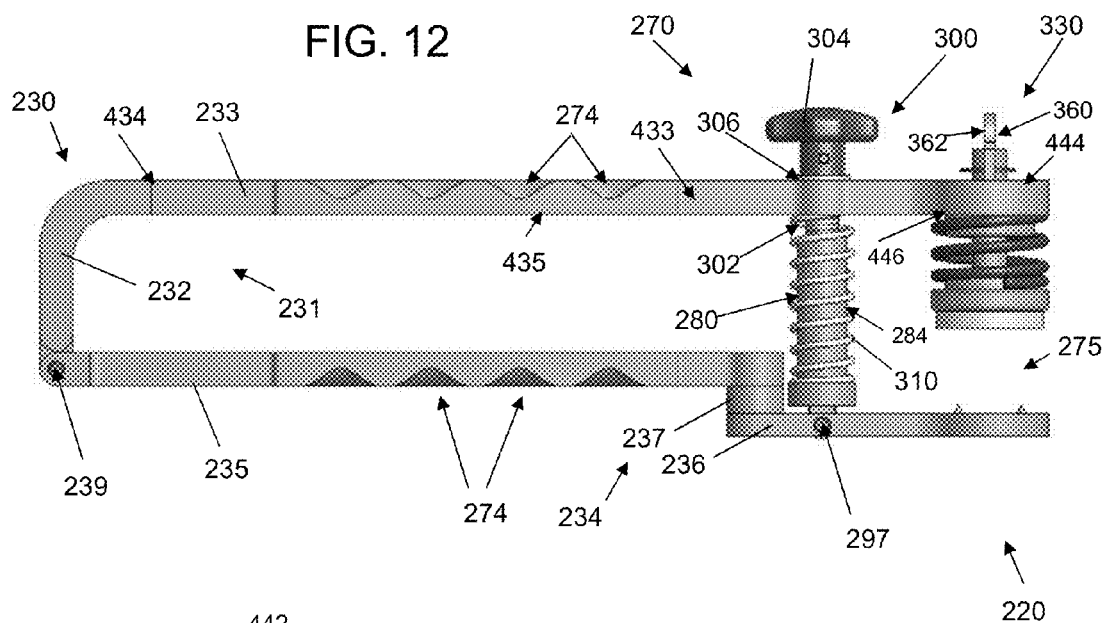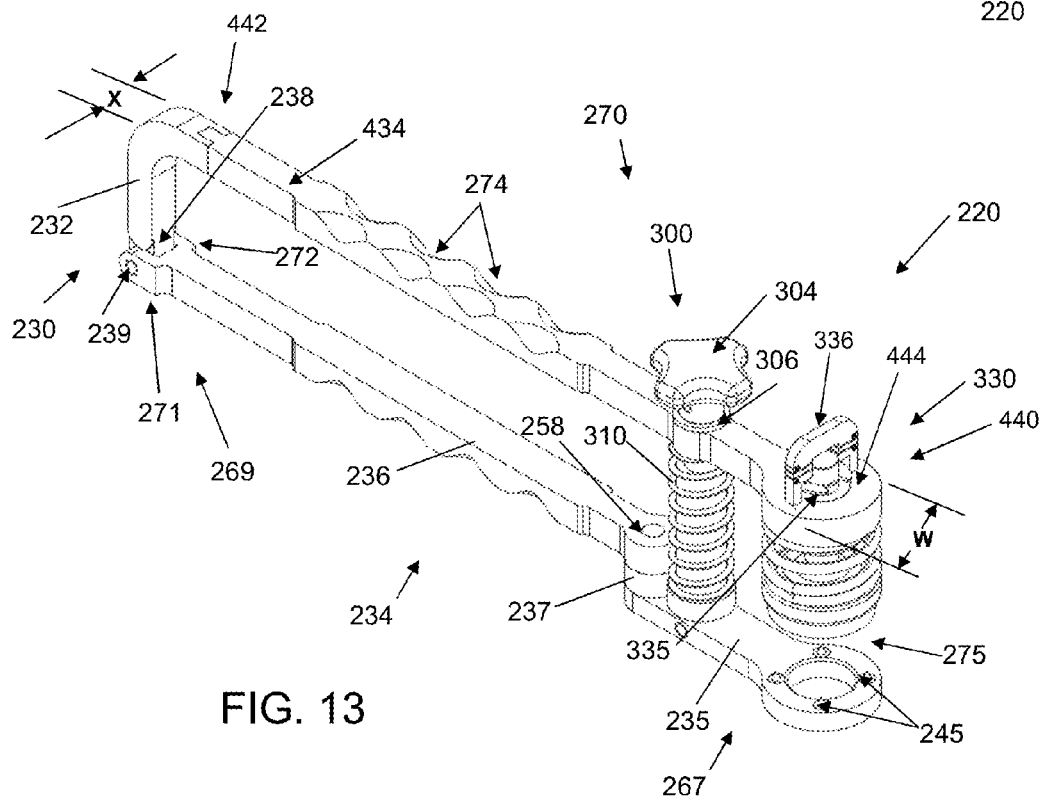

DEVICE FOR FACILITATING ARTIFICIAL PROSTHESIS INSTALLATION WITH MEASURED APPLIED PRESSURE AND METHOD THEREFOR

FIELD OF THE INVENTION

The present invention relates to medical instrumentation, and more particularly to a device for facilitating the installation of an artificial prosthesis and related methods.

BACKGROUND AND SUMMARY OF THE PRESENT INVENTION

Heretofore, no system of instrumentation has been developed which enables a medical professional such as a surgeon to accurately apply specific required measured pressure upon the surgically prepared patella construct to maximize the highest success of the bone cement bond relative to the resurfaced natural patella and the artificial patella replacement and also, indicating known pressure to give mindful consideration to minimize the risk of creating micro-fractures in the host patella.

The typical known art of surgically resurfacing the natural patella, when necessary to accept an artificial patella prosthesis, requires the patella to be everted and held in a position allowing the surgeon to have access to the articulating surface which normally articulates within the intercondylar notch between the femoral condyles.

The natural patella is first measured, establishing its exact thickness, after which the surgeon resects the appropriate thickness of the posterior portion of the natural patella, and then prepares the surface to receive the artificial patella prosthesis. A patella trial replicating the actual implant to be installed is placed upon the prepared patella surface to confirm proper fit and thickness of the patella construct that establishes proper ligamentus tension for optimum stability and range of motion whereupon, a bonding agent (e.g., bone cement) is prepared. In the typical known handling of the bone cement, there is an exact science of measured polymer (e.g., powder) and monomer (e.g., liquid) packaged sterile in their individual respective states delivered into a sterile field placed into and enclosed in a sterile container whereupon measured vacuum force is applied and a measured time of thorough mixing is conducted. The properties are handled under strict scrutiny and respectful disciplines. When the vacuum is released, the top of the sterile container can be removed, giving access to the bone cement, whereupon it is examined to confirm that it is in the proper state to be applied. Precautions are generally taken to create the bone cement and bring it into a proper stable useable product, whereby it can be applied in order to successfully bond the aforementioned surfaces. At this juncture, and in the past art, the typical known patella clamp is applied and a disruption to sound science and respect to mechanical properties of the bone cement occurs, putting the surgeon in an unfortunate place of having to use inadequate instrumentation to carry out this process in respectful consideration of all parameters involved.

In the past, it is known to apply a clamp to the patella construct (which consists of the surgically resurfaced posterior aspect of natural patella prepared to receive an artificial patella replacement paired with the bonding agent bone cement). However, methods and devices for applying the pressure have not been controlled and have resulted in the application of an arbitrary and unknown pressure upon the patella construct until the bone cement is fully cured. As such, less than satisfactory results can occur.

Measured pressure upon the patella construct is a paramount consideration to the mechanical properties, scientific quantitation and increased long-term success of the bonding integrity of the bone cement. Heretofore, no patella clamp has existed for general surgical use which takes into account all the parameters and dynamics taking place within the patella construct as it relates to all surfaces involved and the scientific and mechanical properties of the bonding agent bone cement during installation, as well as, the potential of excessive unknown pressure upon the host patella creating micro fractures.

In various aspects, the present invention enables the medical professional (i.e., surgeon) to accurately apply positive linear directional control and known pressure upon the patella construct throughout the process to the cure state of the bone cement. After the initial proper pressure is established upon the patella construct, certain variables can come into play affecting the applied pressure. In the past, any pressure changes went unnoticed, unknown and/or unaddressed. In various aspects, the present invention allows the attending medical professional(s) to stay informed as to pressure changes, giving the medical professional(s) the capability to re-establish correct pressure by known positive control. As such, various aspects of the present invention bring true reproducible scientific and mechanically responsible practice to the installation of an artificial patella prosthesis in total and partial knee arthroplasty. It will be appreciated that the various aspects of the device and methods described herein are not necessarily limited to applying measured pressure to a patella construct, but may be equally employed in other medical and mechanical applications.

The present invention, in part, brings scientific and mechanical enabling to the surgeon to help create reproducible and successful outcomes. Aspects and embodiments of the current inventive device receive the everted patella in its prepared form whereupon the anterior portion of the natural patella is placed upon a spiked platform of a bottom plate associated with the device. Upon the patella being held in place, the surgeon or other medical professional takes hold of the knob of the knob assembly of the present device, holding it firmly in one hand. With the other hand, the medical professional depresses the quick release button of the present device, freeing the adjustment rod thereupon. As the medical professional pushes downward atop the knob, the indicating assembly of the present device translates downward in a controlled linear direction as its slide ring houses and translates upon the keyed guide rod acting as an established vertical stable construct. When the patella bushing of the present device makes contact with the artificial patella of the patella construct, the medical professional releases the quick release button allowing the adjustment rod threads to functionally engage. The medical professional, with hand upon the assembly knob, turns the knob (e.g., in a clockwise motion), creating a controlled linear downward movement of the indicating assembly generating pressure upon the patella construct. In aspects of the present invention, every clockwise revolution of the knob creates an increase of pressure upon the patella construct. As the controlled pressure is applied, the indicating assembly measures the pressure being applied and an assembly contained calibrated indicator gives visual knowledge and reference as to the precise amount of measured applied pressure being applied.

In alternative embodiments, a medical professional secures an appropriately sized insert into the device, ensures that the everted patella is appropriately situated in the receiving area of the device, adjusts a knob assembly to a desired level associated with a measured pressure.

Upon the surgeon creating the specific required and known applied pressure, the clockwise turning motion upon the assembly knob can be terminated. At this time, the bonding agent within the patella construct will squeegee out; the bottom platform spikes will depress into the anterior patella and the bushing (e.g., a rubber bushing or of other material and design) in the stem of the clamp indicating assembly can settle in. It will be appreciated that the above processes can take effect within seconds and the amount of applied pressure can thereafter decrease.

Thereupon, the present inventive device indicator visually informs the medical professional(s) of the potential adverse change in pressure and this calibrated reference gives the necessary information to correct and re-establish proper pressure. In the event of change from optimum applied pressure, the medical professional can create additional needed known applied pressure by again turning the assembly knob to re-establish the precise prescribed pressure to be upon the patella construct. The present invention thus, in part, enables the medical professional to create and maintain measured applied pressure upon the patella construct until the bone cement is fully cured. Upon the professional confirming the bone cement is fully cured, the present device can be removed by turning the knob in the opposite direction from the direction used to apply pressure, thereby relieving pressure off the indicating device. At such time, the quick release button can be depressed in one embodiment of the present invention, disengaging the assembly rod whereupon the assembly knob can be pulled upward. In this way, the indicating assembly can be quickly advanced up the guide rod to its highest allowable level, after which time the quick release button can be released, whereupon the assembly re-engages the threads of the assembly rod, locking the indicating assembly in place and allowing the removal of the device. In alternative embodiments, no quick release button is employed, and the knob is simply turned sufficiently enough to allow the cured construct to be removed from the device.

Among other things, the present invention revolutionizes the typical known procedure in the installation of an artificial patella prosthetic replacement in total knee arthroplasty and is also introductory to additional improvements within a system of surgical instrumentation.

BRIEF DESCRIPTION OF THE DRAWINGS

FIG. 9 is a perspective view of a top plate according to one embodiment of the present invention.

FIG. 10 is a perspective view of a bottom base plate according to one embodiment of the present invention.

FIG. 11 is a perspective view of a portion of an actuator assembly in accordance with one embodiment of the present invention.

FIG. 12 is a front elevational view of an assembled version of one embodiment of the present invention.

FIG. 13 is a perspective view of the embodiment of FIG. 12.

DETAILED DESCRIPTION OF EMBODIMENTS

Figure 1:
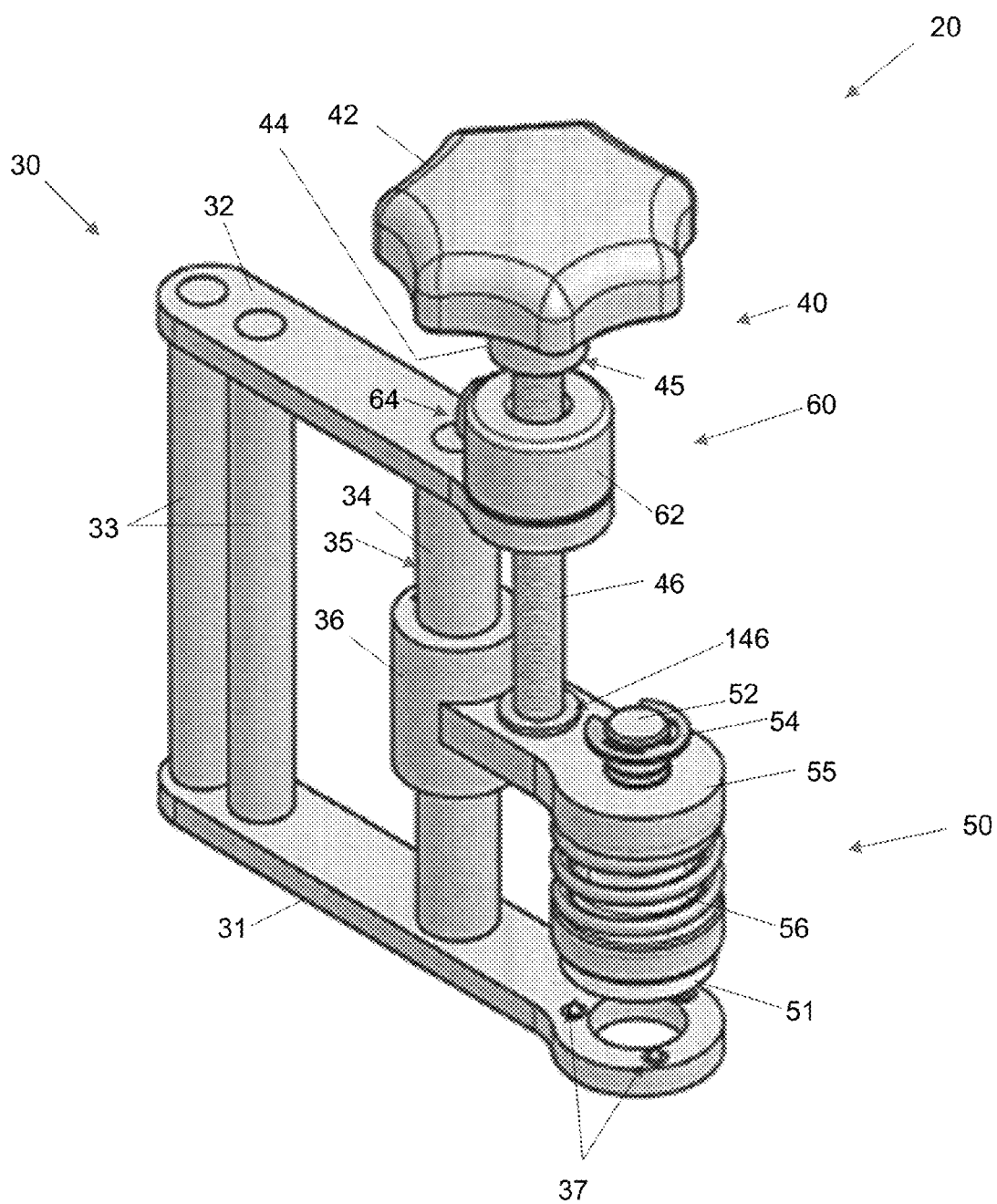
FIG. 1 is a perspective view of an assembled version of one embodiment of the present invention.
Figure 2:
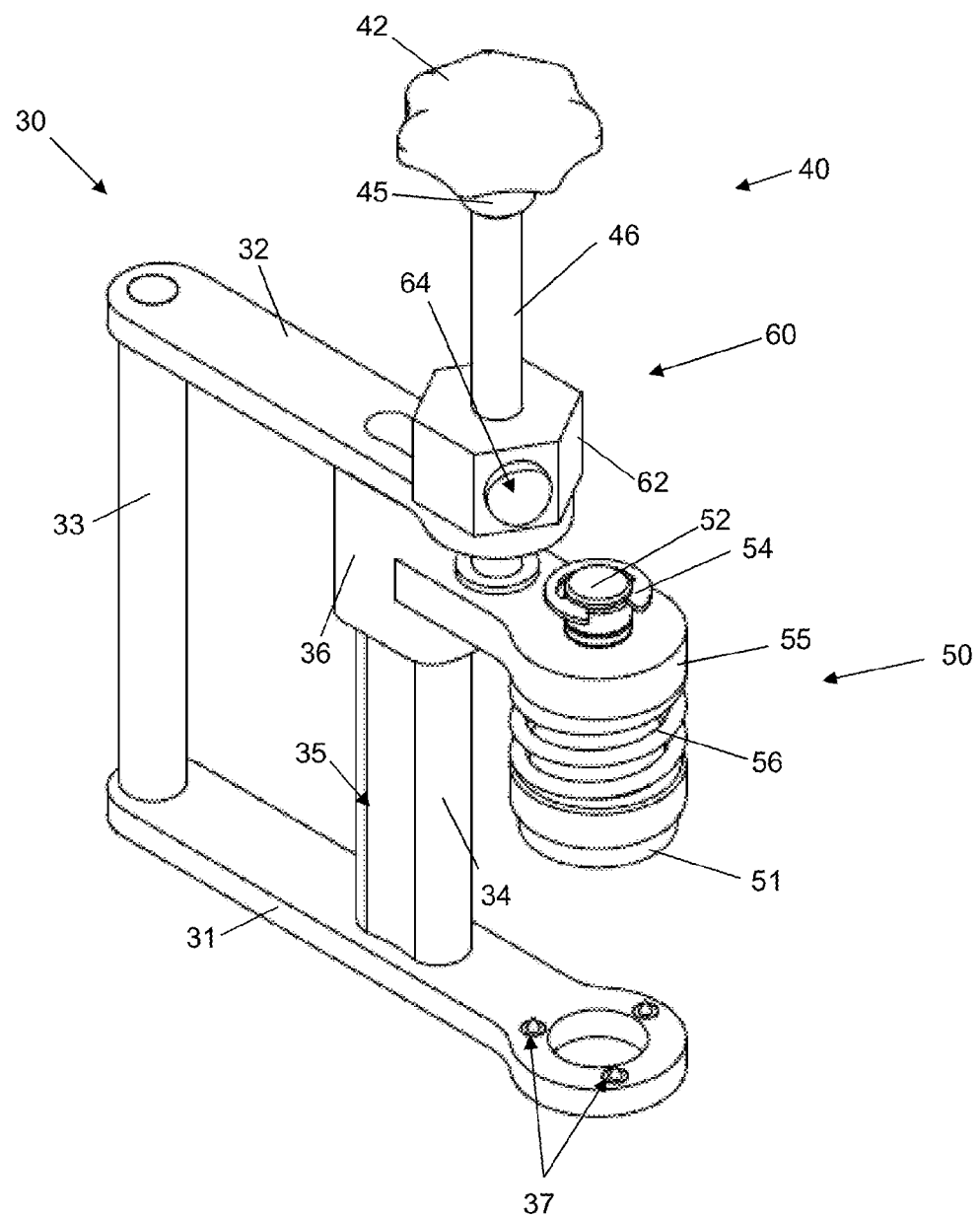
FIG. 2 is a perspective view of an assembled version of an alternative embodiment of the present invention.

FIGS. 1 and 2 are perspective views of different embodiments of the adjustable measured applied pressure clamp device 20 of the present invention. As shown in the embodiment in FIG. 1, the device 20 comprises a frame assembly 30 for receiving and maintaining a knob assembly 40 and a clamp indicating assembly 50.

The frame assembly 30 can comprise a bottom base plate 31 and a top plate 32, which are held apart in substantially parallel relation by a handle member 33 and a guide rod 34. In various embodiments of the present invention, the base plate 31 includes one or more spikes 37 for use in assisting with holding an object being compressed during operation of the present invention. As shown in FIG. 10, openings 131 are provided in the base plate 31 to receive spikes. While the handle member 33 is shown in FIG. 1 as a pair of substantially cylindrical bodies secured to the bottom 31 and top 32 plates, it will be appreciated that the handle member 33 can take various forms without compromising the function of the present invention. For example, as shown in FIG. 2, the handle 33 can be a single member.

In the embodiment shown in FIG. 1, the guide rod 34 is a substantially cylindrical body secured to the bottom 31 and top 32 plates. In the embodiment shown in FIG. 2, the guide rod 34 is somewhat "peanut-shaped" in cross-section and is secured to the bottom 31 and top 32 plates. The guide rod 34 is positioned proximate to the knob assembly 40 and clamp indicating assembly 50, whereas the handle member 33 is positioned away from the knob assembly and clamp indicating assembly 50. The relative positioning of the handle member 33 and the guide rod 34 assists in ensuring that the plates 31 and 32 are maintained in stable position to facilitate operation of the present invention. In various embodiments of the present invention, the frame assembly 30, including the plates 31, 32, the handle member 33 and the guide rod 34 can be formed of stainless steel, aluminum, plastic, brass and other materials of sufficient hardness and strength for the contemplated purposes and operations. Further, the handle member 33 and the guide rod 34 can be secured to the plates 31, 32 by being bolted, welded, soldered, pressed, captured and other known forms of connection. In embodiments of the present invention (see FIGS. 9 and 10, for example), openings 39 in the plates 31, 32 facilitate the connection with the handle member(s) and openings 38 facilitate connection with the guide rod 34.

Figure 3:
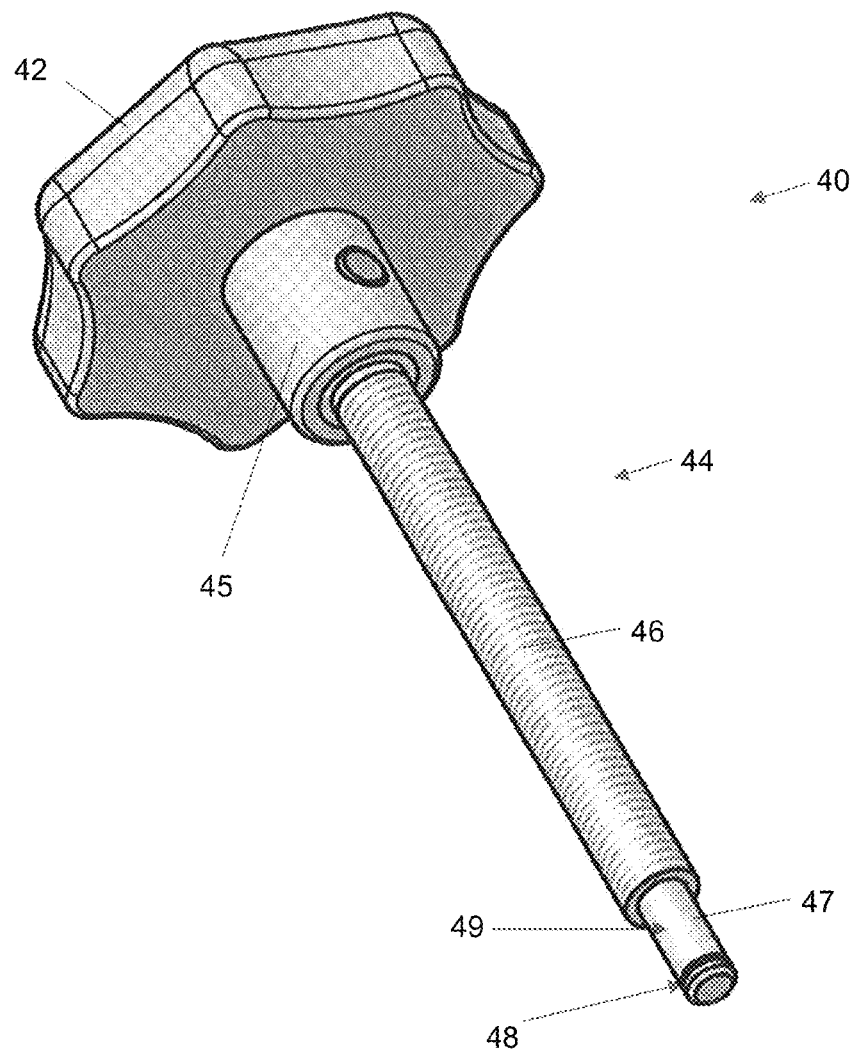
FIG. 3 is a perspective view of a knob assembly portion of one embodiment of the present invention.

As shown in FIGS. 1 through 3, the knob assembly 40 of the present invention can include a knob 42 and an adjustment rod 44. The knob 42 can be attached to the adjustment rod 44 by being pressed, bolted, welded, soldered, pinned, threaded or being integrally formed, for example. The adjustment rod 44 can include a base portion 45, an extension portion 46, and an extension segment 47 having a groove 48 formed in the outer surface 49 thereof. In embodiments of the present invention, the base portion 45 is substantially cylindrical with a substantially smooth exterior and the extension portion 46 is also substantially cylindrical and includes a threaded exterior for engaging an actuator assembly 60 as described in more detail hereafter. The extension segment 47 extends axially outwardly of the extension portion 46 and is adapted to extend through top plate 32, the actuator sleeve 62 and into a slide platform 55 of the clamp indicating assembly 50, as described in more detail hereafter. A locking pin (not shown) can secure the knob assembly 40 to the slide platform 55 by firmly engaging the groove 48 after the extension segment 47 has passed through an opening 53 in slide platform 55 (see FIGS. 5 and 6). In this way, the knob assembly can influence the movement of the slide platform 55 and thus the clamp indicating assembly 50, as described in more detail hereafter.

As shown in FIGS. 1, 2 and 11, the actuator assembly 60 includes an actuator sleeve 62 and an actuator button 64 extending outwardly of the outer surface 63 of the actuator sleeve 62. The actuator sleeve 62 is formed with a substantially cylindrical opening 65 having a diameter D extending axially therethrough, wherein the opening 65 is adapted to receive the extension portion 46 of the adjustment rod 44 of the knob assembly 40. In various embodiments of the present invention, the actuator button 64 is formed in communication with a substantially U-shaped backside ridge (not shown) on the inside of the sleeve 62, such that when the button 64 is at rest, the backside ridge extends radially inwardly of the opening 65, effectively reducing the diameter D of the opening 65. When the button 64 is depressed towards the outer surface 63 of the sleeve 62, the backside ridge on the inside of the sleeve 62 is move radially outwardly, thereby restoring the full diameter D to opening 65 and permitting free axial passage of the extension portion 46 inserted therethrough. When the button is released, the backside ridge engages the extension portion 46 and holds it in axial position until such time as the button is pressed again, or the knob is rotated. When the button 64 is in the relaxed position, the extension portion 46 of knob assembly 60 can still move axially through the opening 65; however, any such movement occurs through rotation of the extension portion 46 using knob 42, for example. In this way, the outer thread of the extension portion 46 threadedly engages the backside ridge of the actuator assembly 60 to thereby move through the actuator sleeve in a more controlled and slower manner than through straight axial movement when the button 64 is depressed. Thus, the height of the clamp indicating assembly 50 above the bottom plate 31 of the frame 30 can be quickly adjusted upwardly and downwardly by depressing the actuator button 64, yet can also be adjusted more slowly and in a finer and more calculated fashion when the button is in the relaxed position and not pressed. It will be appreciated that the actuator assembly 60 can be provided as any of a number of commercially available push-button actuators, and can be secured to an end of the top plate 31 by being bolted, welded, soldered, pressed, captured and through other known forms of connection. It will also be appreciated that the thickness and pitch of the thread can be altered through other designs to suit ergonomic demands. Other devices beyond that shown can be used to accomplish the same or similar functions as assembly 60. In embodiments of the present invention, openings 67 in the sleeve 62 and openings 69 in plate 31 (see FIGS. 9 and 11) facilitate this connection.

Figure 4:
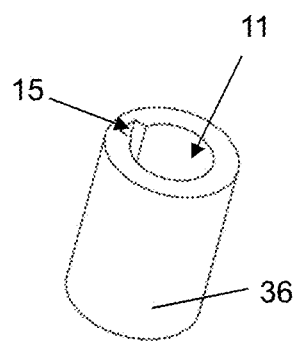
FIG. 4 is a perspective view of a guide rod sleeve of one embodiment of the present invention.
Figure 5:
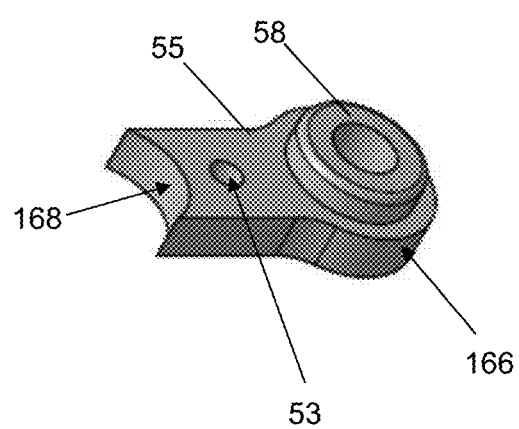
FIG. 5 is a perspective view of a slide platform portion of a clamp indicating assembly according to one embodiment of the present invention.
Figure 6:
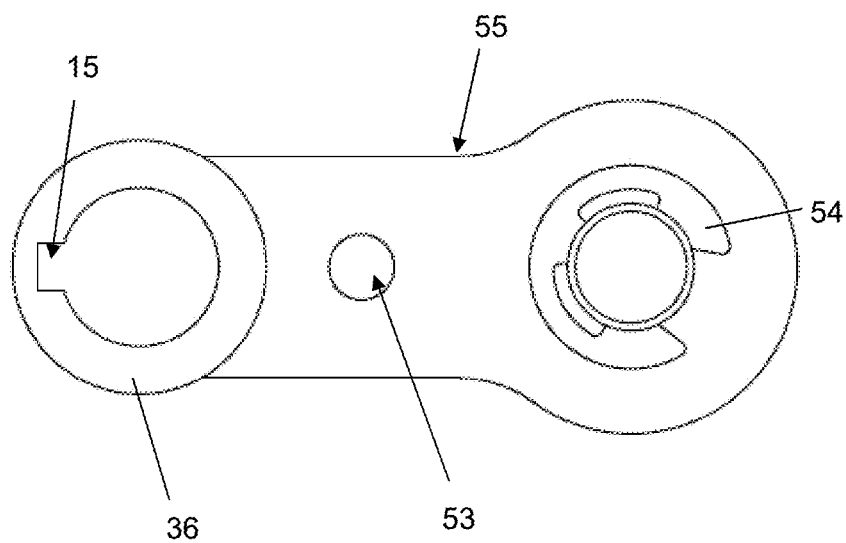
FIG. 6 is a top plan view of elements of a pressure monitor assembly of one embodiment of the present invention.
Figure 7:
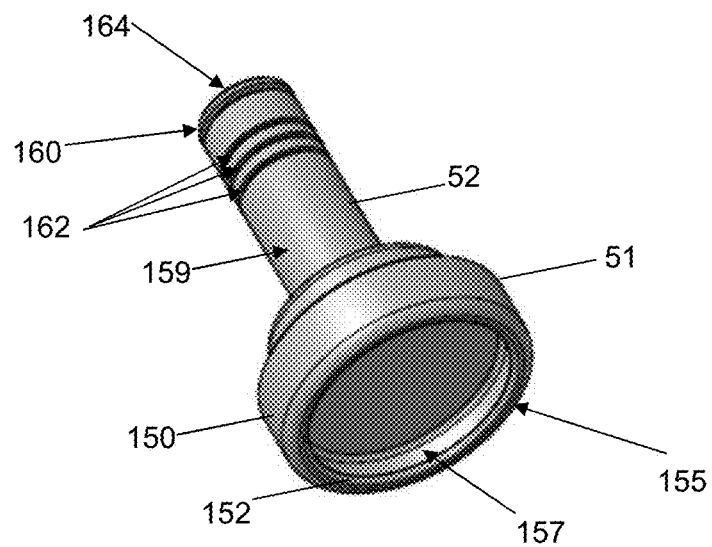
FIG. 7 is a perspective view of a stem assembly portion of a pressure monitor assembly according to one embodiment of the present invention.
Figure 8:
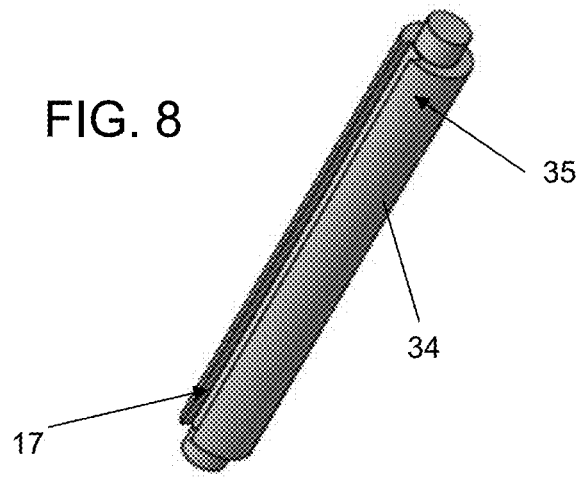
FIG. 8 is a perspective view of a guide rod according to one embodiment of the present invention.

As shown in FIGS. 1, 2 and 4 through 6, the clamp indicating assembly 50 is secured to the knob assembly 40 and the guide rod 34. In various embodiments, the guide rod 34 includes a flange member (not shown) extending radially outwardly along substantially the entire axially outer surface 35 of the rod 34. This flange member is adapted to engage the inner key opening 15 of the guide sleeve 36. In alternative embodiments of the present invention, the guide rod 34 itself is keyed in the sense that it has a groove or depression 17 formed therein (see FIG. 8), wherein the groove 17 extends substantially axially along the outer surface 35 of the guide rod 34. This groove is adapted to receive an extension or flange member (not shown) of the guide rod sleeve 36. In either arrangement, the sleeve 36 can smoothly and movingly engage the guide rod 34 in linear fashion during operation of the present invention as will be described more completely hereafter. As shown in FIGS. 1, 4 and 6, the guide rod sleeve 36 is substantially cylindrical in shape, with an opening 11 extending axially therethrough, which permits the guide rod sleeve 36 to abut the outer surface 35 of the guide rod 34 for moving engagement therewith. It will be appreciated that other shapes of items 34 and 36 can be used to provide a guided single axis linear movement (see, for example, FIG. 2).

As shown in FIGS. 1, 2 and 5 through 7, the clamp indicating assembly 50 of the present invention can comprise a stem 52, a locking C-clip 54, a slide platform 55 and a load spring 56. These components assist in providing a mounting surface for mounting and articulating end effectors such as rubber or other material contactors that are used to press, hold or grip elements to be worked on during operation of the present invention, such as a patella or appliances used to replace portions of the patella, for example. Stem 52 can be used to assist in holding an element in position as additional devices aid in the patella restoration. Stem 52 also provides a bearing surface for linear movement during the function of applying pressure and provides a means of measurement. It can be used to rotate and orientate attachments. It can rotate to allow for easy use in various positions and accommodate left or right handed operators. The stem has a substantially hollow base portion 51 with a "major" or larger inner diameter defined by an outer wall 150 and a "minor" or smaller inner diameter defined by a lip 152 on the axially outer end 155 of the stem. The lip 152 helps to retain a bushing (not shown) inserted into the hollow opening 157 in the base portion 51. As further shown in FIG. 7, the stem includes a body portion outer surface 159 having substantially circumferential grooves 160, 162 formed therein. A first groove 160 is formed at an axially outer end portion 164 of the stem 52 and is cooperatively engageable with a clasping member, such as locking C-clip 54 shown in FIGS. 1 and 2. Other grooves 162 are measurement indicators that assist a user of the device in its various embodiments in understanding the amount of pressure being applied to a subject element, as will be described in more detail hereafter.

As further shown in FIGS. 1, 2, 5 and 6, the clamp indicating assembly 50 includes a slide platform 55 and load spring 56. The spring 56 can be positioned around stem 52, and the stem can then be inserted through opening 53 in the slide platform, after which the clip 54 can be locked into the groove 160 of stem 52. When locked, the stem 52 is then slidably maintained within the slide platform 55, and the clip 54 prevents the stem 52 from sliding all the way through the platform 55. However, the stem can be moved upward as shown in FIG. 1, where space exists between the clip 54 and the platform 55, and back down to a position where the clip 54 is in contact with and directly atop the platform 55, as shown in FIG. 2. In various embodiments of the present invention, as shown in FIG. 5, for example, the slide platform 55 includes a spring guide extension 58 which extends from the inside surface 166 of the platform 55 and acts to retain the spring 56 in fixed radial position, such that the spring can only compress and extend, without moving from side to side. The platform 55 is also provided with a concave end surface 168 which is adapted to mate with the guide sleeve 36 in substantially flush relation. The platform 55 can be secured to the guide sleeve 36 in a variety of ways, including by being bolted, welded, soldered, pressed, captured and using other known forms of connection.

In one embodiment, the present invention provides a method for assembling a device to provide adjustable, measured clamping pressure, including the steps of: Embodiments of the device can be assembled after all manufacture related operations are complete by sliding spring 56 onto stem 52. These are now slid through opening 53 in platform 55 and clip 54 is snapped into the groove 160 on stem 52 creating assembly 50. Assembly 50 can now be slid onto guide rod 34 with the key and the slot aligned, as described above. This sub-assembly can now be set aside. Actuator assembly 60 can then be attached to top plate 32 using flat head screws or other connection, and this sub-portion can then be set aside. Handle member(s) 33 can then be positioned into alignment holes 39 on plate 31 and attached using button head screws or in another fashion. The previously assembled clamp indicating assembly 50 can then be secured to plates 31 and 32 with rod secured within openings 38 of plate 31 and 32. The assembly 50 can be visually aligned above the spikes 37. Now, actuator assembly 60 and knob assembly 40 are installed, and actuator assembly 60 is slid down until the tip of an adjusting screw is slightly above part 55. In various embodiments, an installer can visually make sure the tip of extension portion 46 of rod 44 aligns with the opening 53 in slide platform 55. A thrust washer 146 can then be installed onto the end of extension portion 46 (above the slide platform 55) and a locking clip installed underneath and into groove 48. The guide rod sleeve 36 should smoothly slide up and down on guide rod 34 when actuated by turning knob 42. When all alignment is established, any untightened connectors can be tightened as appropriate.

In exemplary embodiments of operation of the device of the present invention, one can assume that a body part, such as the patella of a human knee, is being replaced or repaired. With the various embodiments of the present invention, measured pressure can be applied and accurate positioning accommodated in restoration of the patella, for example. In various aspects, other attachments to plate 31 or assemblies 50 and/or 60 can aid this and other surgeries where accurate pressure and positioning are needed. Other embodiments of the present invention can be incorporated into or become new devices improving or replacing existing devices that now are outdated for their original purpose.

In a specific embodiment of operation, a medical professional such as a surgeon grasps the knob 42 of the knob assembly 40, then depresses the quick release button 64 on the actuator assembly 60. Upon depressing the quick release button 64, the adjustment rod 44 which passes through the actuator 62 and the top plate 32, and whose distal tip passes through the horizontal slide 55 is locked in place therein, is freed, allowing the slide 55 to translate vertically and parallel to the guide rod 34. This motion continues until the patella mating bushing attached to the base part 51 of the stem 52 makes direct contact with the artificial patella prosthesis. Upon full contact, the quick release button 64 is released, causing the thread engagement of the adjustment rod extension portion 46, whereupon the surgeon grasping the knob 42 can turn the knob in a clockwise motion, creating a controlled downward movement generating pressure upon the patella construct.

In fluid sequence, the stem portion 52 is then set and fixed upon the patella construct, passing through the load spring 56 which butts up on the horizontal slide 55 and the stem continues up through the horizontal slide 55 and is secured by a locking clip 54 at the most proximal part of the stem 52.

The artificial patella construct generally comprises an artificial patella prosthesis, followed by a bonding agent, followed by a natural patella that has been re-surfaced for facilitating best results in the knee replacement operation. The artificial patella prosthesis is positioned at the bottom of the clamp (in between the base plate 31 and the stem head 51. Then, the bonding agent, such as bone cement, is applied, and the natural resurfaced patella is then placed atop the bonding agent. Appropriate pressure must then be applied to properly secure the artificial patella prosthesis with the natural patella.

The first segment of the clamp indicating assembly to make contact with this patella construct is the bushing (not shown) which can be, for example, of a rubber material in a circular design to receive a button style artificial patella prosthesis. Other contact bushings of materials of plastic, metal and other designed to accept the geometric configuration of any artificial patella prosthesis replacement can be installed into the base 51 to facilitate operation of the present invention. The major inner diameter of the base 51 (described above) which receives the appropriate bushing and the minor diameter (described above) form an inner rim to serve as a locking mechanism to hold the specifically designed bushing securely in place. The stem grooves 162, which have been mathematically placed to serve as reference points for measuring pressure.

As the clamp indicating assembly 50 makes contact with the patella construct, the spikes 37 can engage the patella to hold it in place. As the surgeon continues to turn the knob 42 in clockwise motion, more pressure is evenly applied upon the construct, as the downward motion of the operative parts bear down, and the load spring 56 is compressed. As the load spring is compressed along with the respective assemblies moving downward, the stem proximal portion begins upward movement through the bore 53 of slide platform 55 as described above. The reference markings provided by grooves 162 indicate the exact measurement of pressure being applied. When the prescribed rate of pressure is achieved by the actions of the surgeon, the device can be held in position at the desired pressure for the desired length of time.

It will be appreciated that the present invention establishes the proper amount of measured applied pressure upon the patella construct on all involved and necessary surfaces. So after the initial establishment of pressure, all surfaces settle in the bone cement. To the extent the elements being compressed cause the pressure to change after initially being set, the pressure can be re-established. This is immediately revealed by visual assessment of the indicator grooves 162 of the device, which has not been available heretofore. Now a failure mode can be scientifically detected and mechanically corrected. The surgeon simply upon viewing the deficiency through the indicator grasps handle 33 in one hand and grasps knob 42 in the other, turning the knob in a clockwise motion with micro adjustment, thereby establishing or re-establishing the exact recommended pressure. The surgeon waits for full cure of the bones cement, and can verify this thereafter. To remove the device, the surgeon takes hold of handle 33 in one hand and grasps knob 42 with the other hand and turns the knob in counter clockwise motion to relieve the initial pressure of the device. Then with the hand that is on the handle 33, the surgeon can depress the quick release button 64 and pull straight up on knob 42, then release button 64 as the assembly locks in place. The device can then be removed.

It will be appreciated that aspects of the present invention can be provided such that the apparatus is "pre-set" to a desired or industry known or required pressure using a single action, such as by using actuator button 64.

FIGS. 12 through 21 show elements according to different embodiments of the adjustable measured applied pressure clamp device of the present invention. As shown in the embodiment in FIG. 12, the device 220 comprises a frame assembly 230 for receiving and maintaining a clamp assembly 270, which can include a knob assembly 300 and a pressure monitor assembly 330.

The frame assembly 230 can include an upper frame arm 231 and a lower frame arm 234. In various embodiments, the upper frame arm 231 and lower frame arm 234 comprise independent monolithic units. In other embodiments of the present invention, the upper frame arm 231 and lower frame arm 234 can comprise multiple elements. The upper frame arm 231 can be referred to herein as an upper frame arm assembly and the lower frame arm 234 can be referred to herein as a lower frame arm assembly, regardless of whether each comprises a single monolithic unit or a multi-element arrangement. As shown, for example, in FIGS. 12 and 13, the lower frame arm assembly 234 comprises a fixed end element 235, a bottom handle element 236 and one or more spacer elements 237. As shown in FIG. 17, for example, the fixed end element 235 is provided with an extension portion 240, a clamp support portion 242, a top surface 244 and a bottom surface 246, with the top surface 244 of the clamp support portion 242 adapted to receive one or more spike elements 245 for receiving and securing elements of a patella construct or other item to be clamped or otherwise manipulated in the receiving area 275, in accordance with the present invention. For instance, the top surface 244 of the clamp support portion 242 can be provided with openings 248 that either extend through the fixed end element 235, or that are provided as blind holes that do not extend through the fixed end element 235, but which can securely receive the spike elements 245. The fixed end element 235 is also provided with a slot 250 extending through the top 244 and bottom 246 surfaces of the extension portion 235, and further a side opening 252 extending from a first side wall 254 to a second side wall (not shown) of the fixed end element 235, and passing through the slot 250. The slot 250 is adapted to receive a pivot nut 280 as shown in FIGS. 12 and 13, for example, and the pivot nut 280 is movably secured to the extension portion 240 of the fixed end element 235. With reference to FIGS. 12 through 17, in various embodiments, a pin 297 extends through the side walls (e.g., first side wall 254) and through an opening 296 in the pivot nut collar 294 when the pivot nut 280 is in position within the slot 250, in order to permit the pivot nut 280 to pivot during operation of the present invention.

As shown in FIG. 13, for example, the spacer element 237 can be provided with a substantially cylindrical body portion having an opening (not shown) therethrough for receiving a substantially cylindrical peg element 258. Alternatively, the peg element 258 and the spacer element 237 can be integrally formed as a monolithic unit. The peg element 258 is appropriately sized so as to be insertable within an opening 241 in the extension portion 240 of the fixed end element 235, and within an opening in the bottom handle element 236. In this way, the spacer element 237 helps secure the bottom handle element 236 to the fixed end element 235, and helps align the receiving area 275 of the device with the axis of the handle element 236. In this way, for example, the principles of operation of the present invention are enhanced. It will be appreciated that various embodiments of the present invention operate with multiple spacer elements such as element 237 in order to increase the area of the receiving area 275 for various sizes of articles and elements to be engaged in accordance with aspects of the present invention. In various embodiments where multiple spacer elements are employed, the spacer elements can be provided such that the peg element (e.g., 258) extends from an interior point within the opening of the cylindrical body portion to an external point outside of one side of the spacer element (e.g., 237). In this way, arrangements with multiple spacer elements can engage in a nested relationship, as a peg from a first spacer element is inserted into an opening of a second spacer element, and the peg from the second spacer element is inserted into the bottom handle element 236, the fixed end element 235, or another spacer element according to the employed arrangement.

As shown in FIGS. 12 and 13, the rear portion 269 of the lower frame arm assembly 234 is hingedly connected to the upper frame arm 231. The upper frame arm 231 can comprise a single monolithic arm, and can alternatively comprise a curved handle section 232 and a straight handle section 233, among other embodiments. The upper frame arm 231 can be hingedly secured to the lower frame arm assembly 234 in various ways. As shown in FIG. 13, for example, the curved handle section 232 of the upper frame arm 231 has a base portion 238 having an opening therethrough, which can receive a pin 239 that extends through edges 271, 272 of the rear portion 269 of the bottom handle element 236. As shown in FIGS. 12 and 13, the straight handle section 233 of the upper frame arm 231 and the bottom handle element 236 can further be provided with indentations or other forms of gripping elements 274 to facilitate operation. The straight handle section 233 includes side wall surfaces 433, a top surface 434 and a bottom surface 435, and in various embodiments, the indentations 274 are on one or more of the side wall surfaces 433.

Figure 15:
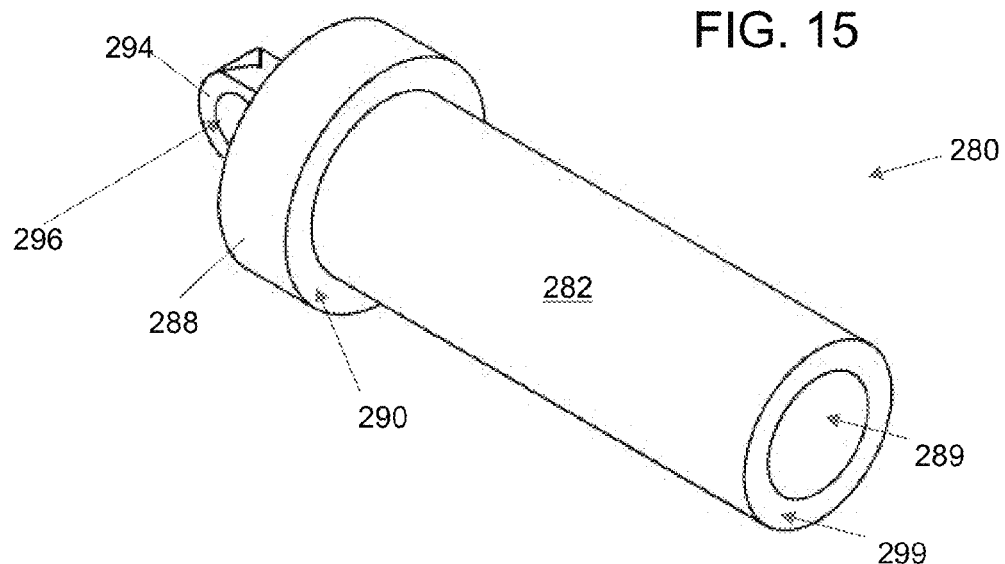
FIG. 15 is a perspective view of a pivot nut element according to one embodiment of the present invention.
Figure 16:
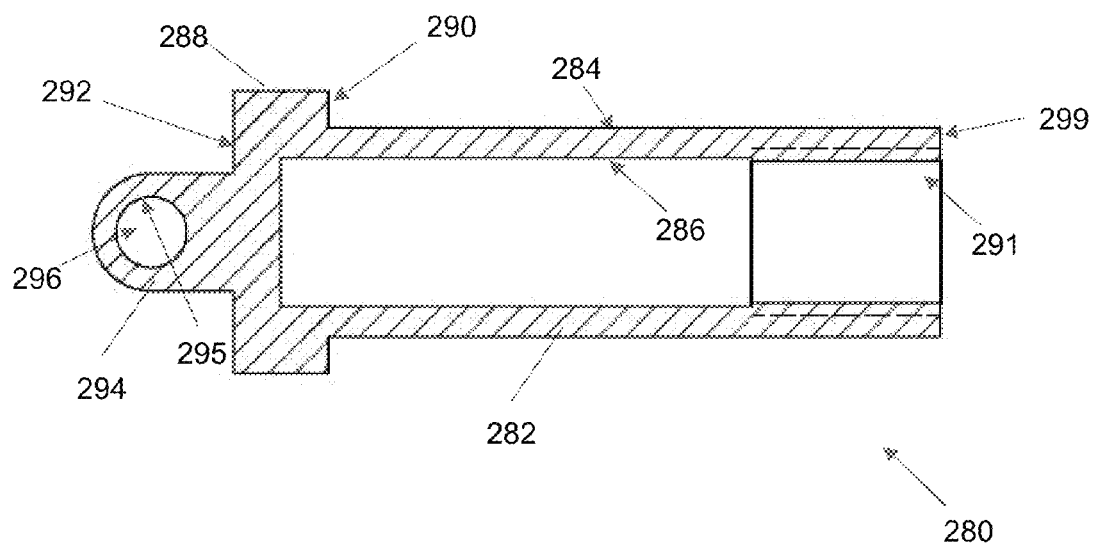
FIG. 16 is a front elevational view of the pivot nut element of FIG. 15.
Figure 17:
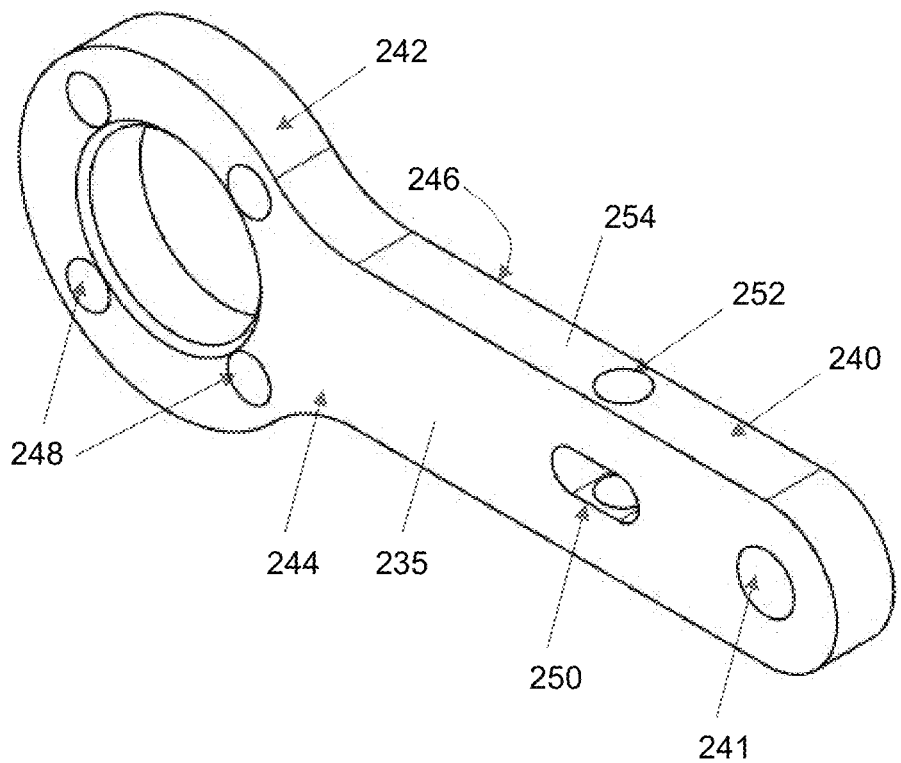
FIG. 17 is a perspective view of a bottom base plate according to one embodiment of the present invention.
Figure 18:
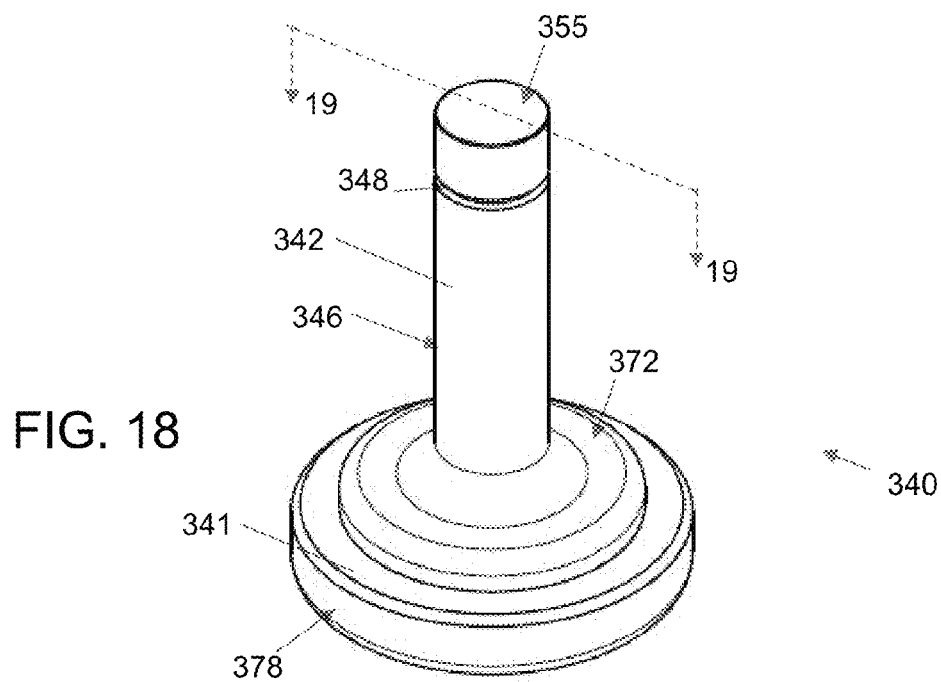
FIG. 18 is a perspective view of a clamp stem element according to one embodiment of the present invention.
Figure 19:
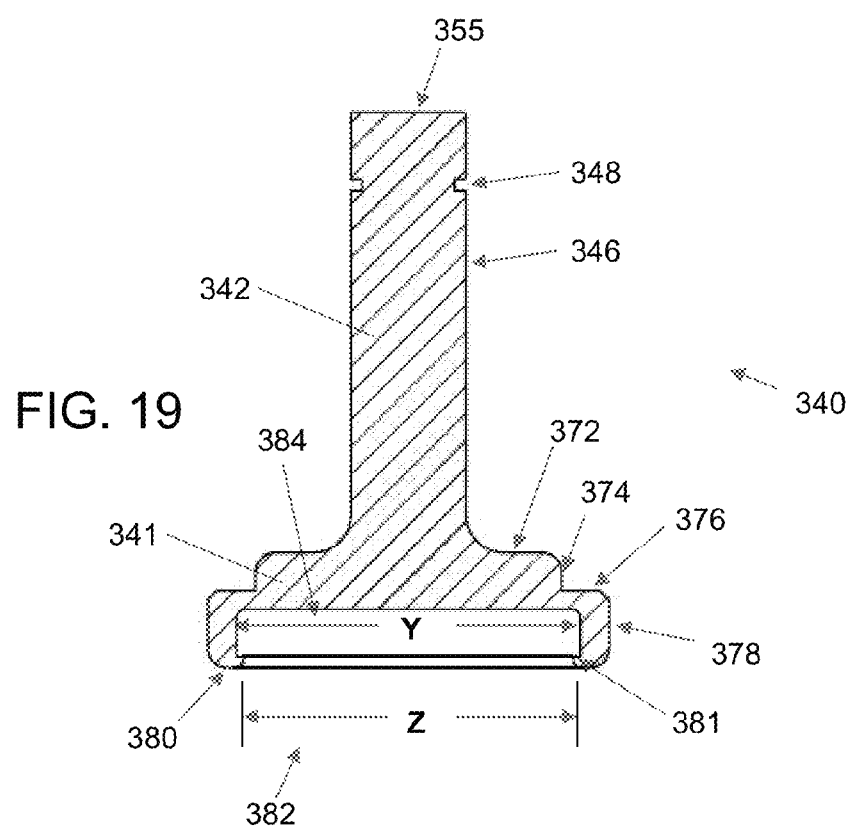
FIG. 19 is a cross-sectional view of the clamp stem element taken along the line 19-19 of FIG. 18.

As shown in the embodiments of FIGS. 12, 13, 15 and 16, the clamp assembly 270 includes a pivot nut 280, a knob assembly 300 and a spring member 310, with the pivot nut 280 pivotally secured to the fixed end element 235 at the front portion 267 of the lower frame arm assembly 234, as described above. In various embodiments, the spring member 310 and the pivot nut 280 can be considered part of the knob assembly 300 of the device of the present invention. As shown in FIGS. 15 and 16, the pivot nut 280 includes a substantially cylindrical body portion 282 having an exterior wall 284 and an interior wall 286, with the interior wall 286 forming an opening 289 in the body portion 282. In various embodiments, the axially outer portion 291 of the interior wall 286 is threaded so as to be capable of threadedly receiving an adjustment screw portion 302 of the knob assembly 300. In other embodiments, the full interior wall 286 is threaded. For example, the interior wall 286 can have a single female receiving thread extending the length of the wall, adapted to receive a male thread on the outer surface of the adjustment screw 302 (see FIG. 12). The threaded engagement of the adjustment screw portion 302 of the knob assembly 300 with the interior 286 of the pivot nut body portion 282 permits the embodiments of the present invention to operate so as to provide increasing or decreasing clamping pressure to the article in the receiving area 275, for example. As further shown in FIGS. 15 and 16, the pivot nut 280 includes a head portion 288 having a head surface 290 and a bottom surface 292, with a pivot collar 294 extending from the bottom surface 292. The pivot collar 294 can be substantially U-shaped in cross-section, with a gap 296 provided between the inner surface 295 of the pivot collar 294 and the bottom surface 292 of the pivot nut head 294. The gap 296 can receive the pin member 297 described above in order to permit the pivot nut 280 to pivot about the fixed end element 235. The pivot nut 280 is further provided with a receiving end 299, which can abut the bottom surface 435 of the upper arm 233 to provide a resistive surface to the knob assembly 300 when the knob 304 is being turned so as to tighten the clamping force on the object in the receiving area 275.

As shown in FIGS. 12 and 13, the adjustment screw 302 of the knob assembly 300 extends through an opening (not shown) in the upper frame arm 233 and engages the pivot nut 280. The knob assembly 300 further includes a knob 304 and a washer element 306. The knob 304 is securable to the adjustment screw 302, such that rotation of the knob 304 in one direction (e.g., clockwise) results in a tighter engagement of the screw 302 with the pivot nut 280, and rotation of the knob 304 in the opposite direction (e.g., counterclockwise) results in a loosening of the engagement between the screw 302 and pivot nut 280. Loosening thereby permits the upper arm 233 to raise higher, thereby permitting more space in the receiving area 275. As further shown in FIGS. 12 and 13, the spring member 310 can be positioned about the exterior wall 284 of the pivot nut body 282, engaging the head surface 290 of the pivot nut head portion 288, and also engaging the bottom surface 435 of the upper arm 233.

Figure 14:
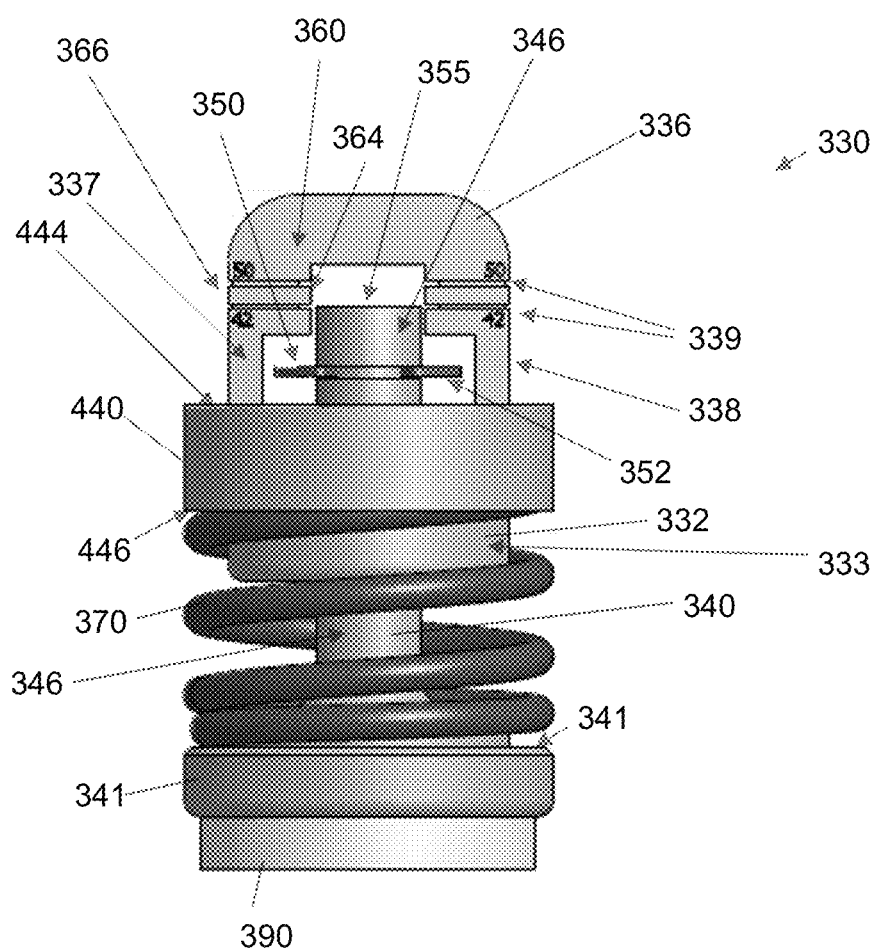
FIG. 14 is a front elevational view of a pressure monitor assembly according to one embodiment of the present invention.

As shown in the embodiments of FIGS. 12, 13 and 14, the upper frame arm 233 has a tip portion 440 formed at the end opposite the rear portion 442. The tip portion 440 can be formed in various shapes, and in various embodiments, can have a top face 444 having a width W that is wider than the width X of the top surface 434 of the upper frame arm 231. In this way, the tip portion 440 is suited to support the pressure monitor assembly 330. The tip portion 440 can be provided with an interior wall (not shown) forming an opening (not shown) in the tip portion 440 for receiving a trunk portion 335 of a clamp stem bushing 332 of the pressure monitor assembly 330. The upper frame arm tip 440 includes a top surface 444 and a bottom surface 446, and the pressure monitor assembly 330 includes a force indicator element 336 secured to and extending from the top surface 444 of the upper frame arm tip 440. As further shown in FIGS. 12 through 14, 18 and 19, the pressure monitor assembly further includes a clamp stem 340 having a base portion 341 and a stem portion 342, wherein the stem portion 342 is extendable through a central opening in the clamp stem bushing 332 and the upper frame arm tip portion 440, so as to be retained in movable relation therein. It will be appreciated that the clamp stem bushing 332 can be formed with a base portion 333 and a trunk portion 335, with the trunk portion 335 having an interior wall forming a substantially cylindrical channel therethrough for receiving the stem portion 342 of the clamp stem 340. The base portion 333 of the clamp stem bushing 332 can be appropriately sized to act as an alignment element for spring 370 when assembled and in operation. The stem portion 342 of the clamp stem 340 includes an outer wall 346, with a ridge 348 formed in the outer wall 346. The pressure monitor assembly 330 further includes a ring clip member 350 positioned within the ridge 348, wherein the ring clip member 350 includes a lower surface 352 engageable with the top surface 444 of the upper frame arm tip 440 and/or the trunk portion 335 of the clamp stem bushing 332. In this way, when the ring clip member 350 is engaged with the top surface 444 of the upper frame arm tip 440 and/or the trunk portion 335 of the clamp stem bushing 332, the device will have a pressure reading of zero. However, and as clamping action occurs on an element within the receiving area 275, the ring clip member 250 will rise from the top surface 444 and/or trunk portion 335, and the top edge 355 of the clamp stem portion 342 will rise to a measurable position proximate the force indicator element 336 secured to and extending from the top surface 444 of the upper frame arm tip 440.

As shown in the embodiments of FIGS. 12 through 14, the force indicator element 336 can be substantially U-shaped with a first arm 337 and a second arm 338 secured to the upper surface 444 of the upper frame arm tip 440, and further wherein the force indicator element 336 includes at least one insignia form 339 on at least one of the first 337 and second 338 arms. In various embodiments, each of the first 337 and second 338 arms includes a front face 360, a back face 362, an interior face 364 and an exterior face 366. Further, the insignia form 339 can be provided on one or more of the front face 360, back face 362, interior face 364 and exterior face 366 of one or both of the first 337 and second 338 arms. The insignia form 339 provides a mechanism for determining the amount of pressure being applied to an article in the receiving area of the device. For instance, the location of the clamp stem portion top edge 355 in relation to the insignia form(s) 339 can be viewed from all around the device, thereby permitting one or more individuals involved in the operation of the present invention to visually determine and measure the amount of pressure being applied to an article in the receiving area of the device. It will be appreciated that the insignia form can be one of many forms of marking, including a physical marking distinguished from the color or shade of the force indicator element 336, as well as a defacement and or indentation on the force indicator element 336.

As further shown in FIGS. 12 through 14, 18 and 19, the pressure monitor assembly can further comprise a pressure monitor spring member 370 positioned around the clamp stem 340 and between the top surface 372 of the clamp stem base portion 341 and the bottom surface 446 of the upper frame arm tip 440. The spring 370 assists in measuring the applied pressure to the article in the receiving area 275.

Figure 20:
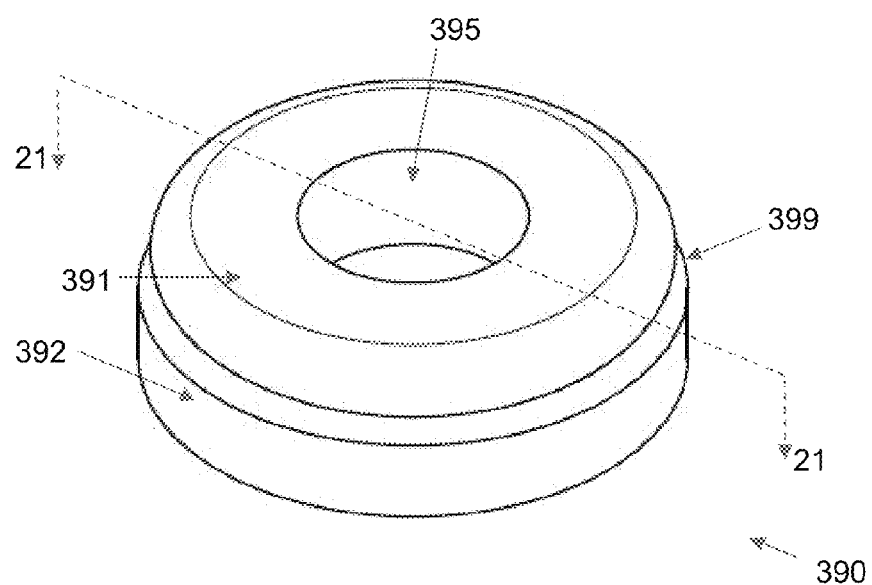
FIG. 20 is a perspective view of a clamp stem insert element according to one embodiment of the present invention.
Figure 21:
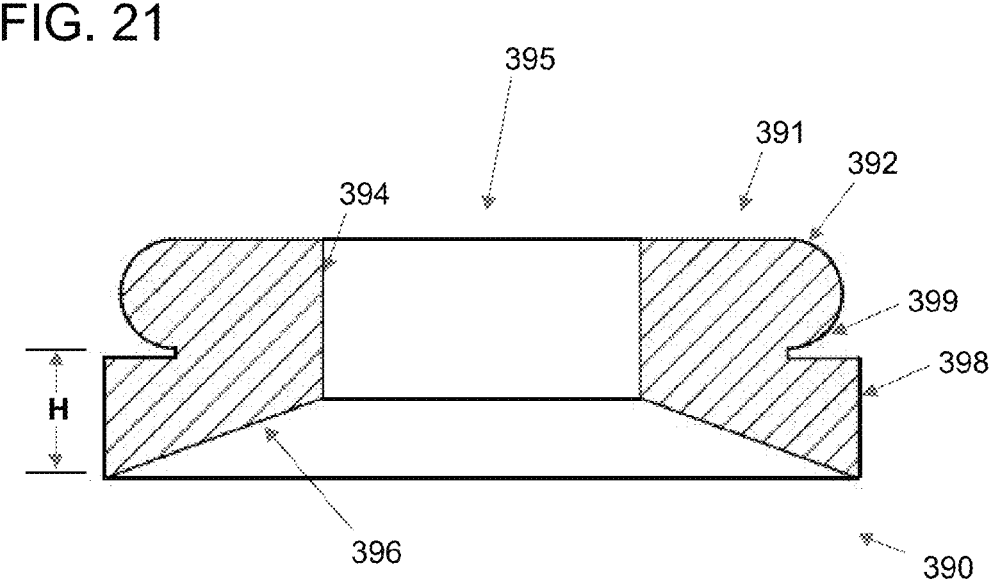
FIG. 21 is a cross-sectional view of the clamp stem insert element taken along the line 21-21 of FIG. 20.

As further shown in FIGS. 14 and 19 through 21, the clamp stem base portion 341 of the clamp stem 340 can be provided with a top surface 372, top surface side wall 374, intermediate surface 376, intermediate side wall 378 and a bottom surface 380, wherein the bottom surface 380 has an opening 382 formed therein so as to form a compartment 384. In various embodiments, the bottom surface 380 has an internal radius Z, and the compartment 384 has an internal radius Y, wherein the compartment internal radius Y is larger than the bottom surface internal radius Z so as to permit the clamp stem 340 to retain various inserts, such as insert 390 in FIGS. 20 and 21. As shown therein, insert 390 includes a top surface 391, an exterior ledge 392, an exterior base surface 398, a bottom surface 393, a top interior surface 394 and a bottom interior surface 396. In various embodiments, the top interior surface 394 is substantially cylindrical in shape, and the bottom interior surface 396 is substantially frustoconical in shape, with both interior surfaces 394, 396 forming an opening through the body of the insert 390. The exterior ledge 392 can be substantially rounded as shown in FIGS. 20 and 21, and a catching notch 399 can be formed between the ledge 392 and the base surface 398 such that, when the insert 390 is positioned into the compartment 384 of clamp stem 340, the catching notch 399 can engage the bottom surface lip 381 to snugly retain the insert 390 within the compartment 384. The varying shapes of the ledge 392, base surface 398 and interior surfaces 394, 396 can assist with the deformability of the insert 390 to adapt to various uses as the insert 390 is deployed within the receiving area 275 of the device. The base surface 398 of the insert 390 has a height H that represents the length of the insert that is exposed beyond the side wall 378 of the clamp stem 340.

Assembly of the embodiments of the invention shown in FIGS. 12 through 21 can occur in several ways. Illustratively, the upper arm 231 and lower arm assembly 234 can be assembled and connected in hinged fashion as described above, wherein the upper arm can comprise a unitary body member, or alternatively can comprise a curved handle section 232 attached to a straight handle section 233. The lower arm assembly 234 can comprise a unitary body member, or alternatively an arrangement including a fixed end element 235, a bottom handle element 236 and one or more spacer elements 237. The fixed end element 235 can be joined with the one or more spacer elements, which are then joined with the bottom handle element. The pivot nut 280 can then be pivotally connected to the fixed end element 235 using pin 297, with the spring 310 inserted over the outer surface 284 of the pivot nut 280. Knob assembly 300 can comprise knob 304 passing through washer 306, with the threaded screw portion 302 of the knob assembly passing through the upper arm assembly 231 and into the pivot nut body portion, where the screw portion 302 can threadingly engage the pivot nut 280. In this way, the upper frame arm and lower frame arm assembly can be locked in a specific location and force can be applied therebetween.

The pressure monitor assembly 330 can then be affixed to the clamp assembly in various fashions. For instance, an insert 390 can be pushed into the compartment 384 of the clamp stem 340. The clamp stem bushing 332 can be fitted and secured through the opening in the upper arm tip portion 440, such as through welding, glue or other methods, the spring 370 can be placed around the stem portion 341 of the clamp stem 340, as well as around the base portion 333 of the clamp stem bushing 332, and the clamp stem 340 can then be fitted through the stem bushing. Once the clamp stem 340 is through the upper arm tip portion 440, the ring member 350 can be secured within the ridge 348 of the clamp stem 340, thereby keeping the clamp stem secured to the upper arm tip portion as the lower surface 352 of the ring member 350 contacts the top surface 444 of the upper arm tip portion 440. The force indicator 336 can then be affixed to the upper arm tip portion 440. It will be appreciated that the above described illustrations of assembly can be performed in a variety of ways, and the particular order of operation described above is not the sole order for assembly.

In operation of the embodiments of the invention shown in FIGS. 12 through 21, an article to be clamped, such as a patella construct, can be placed in the receiving area 275 of the clamp device. In various embodiments, the article is first measured so as to determine an appropriately sized insert 390 to employ. For instance, a thin article may require a larger insert 390, whereas a thicker article may require a smaller insert 390. In various embodiments of the present invention, multiple inserts 390 of different heights H are employed and can be interchanged within clamp stem 340. For example, a first size insert can be provided with a height H ranging from approximately 25.5 mm to approximately 30 mm, a second size insert can be provided with a height H ranging from approximately 21 mm to approximately 25 mm, and a third size insert can be provided with a height H ranging from approximately 15 mm to approximately 20.5 mm. it will be appreciated that the inserts may be provided with different heights H, with broader dimensional ranges of height H, with tighter dimensional ranges of height H, as a set of two inserts, three inserts, or any number of inserts deemed appropriate for a given application.

A portion of the article may be placed on the spike elements of the fixed end element 235 of the lower arm assembly 234. A medical professional, after any necessary intermediate steps, such as securing bone cement or performing some other process on the article, can then rotate the knob 304 so as to bring the pressure monitor assembly 330 onto the article and/or to apply additional pressure on the article. In this way, the upper frame arm and lower frame arm assembly can be locked in a specific location and force can be applied therebetween. The dual spring action of spring 310 about the pivot nut 280 and spring 370 about the clamp stem 340 acts to resist the tension being applied by the user. Once sufficient pressure is applied to the article, any additional force applied through the knob assembly 300 will result in the clamp stem 340 extending upwardly through the upper arm tip portion 440, whereby the top edge 355 of the clamp stem portion 342 will rise to a measurable position proximate the force indicator element 336 secured to and extending from the top surface 444 of the upper frame arm tip 440. It will be appreciated that the location of the clamp stem portion top edge 355 in relation to the insignia form(s) 339 can be viewed from all around the device, thereby permitting one or more individuals involved in the operation of the present invention to visually determine and measure the amount of pressure being applied to an article in the receiving area of the device. Once the top edge 355 is at a desired measured pressure, as indicated by its location adjacent the insignia form(s) 339, the professionals can monitor the pressure to ensure that any pressure adaptations necessary for the required environment can be exacted through the knob assembly. For instance, if a particular procedure requires that forty-two pounds of pressure be applied for seven minutes, and if the pressure reaches a measurement of forty-two pounds for one minute, then begins to drop, the user can rotate the knob 304 to add pressure, and watch the clamp stem portion top edge 355 to ensure it reaches the forty-two pound line on the indicator 336. Similar monitoring and adjustments can occur through the seven minute duration, or whatever duration is required for a particular procedure. When the procedure is complete, the device can be loosened through the knob assembly, and the knob can even be substantially or even entirely disengaged from the pivot nut if necessary to allow an article to be properly removed from the receiving area.

It will be appreciated that the present invention can provide different forms of gauging pressure, including a light-emitting diode (LED) or other visual indicator, an auditory indicator, or other form of indicator in lieu of or in addition to the pressure indicating element 336 shown and described herein. It will also be appreciated that various embodiments of the present invention can employ air, water, nitrogen and other fluids in applying hydraulic pressure. Further, the present invention is adaptable to incorporate electrically and/or battery-powered elements to apply and remove pressure. In still other embodiments, plasma pressure, CNC technologies and/or photoelastics can be employed. Additionally, the assembly of the present invention incorporating the upper and lower arm assemblies can be adapted to implement and measure a pulling force, to the extent a pulling force is desired on a given article instead of a clamping force.

It will further be appreciated that various embodiments of the present invention can employ various material types, including but not restricted to stainless steel, aluminum, brass, plastics and high strength composites, for example.

The invention may be embodied in other specific forms without departing from the spirit or essential characteristics thereof. The present embodiments are therefore to be considered in all respects as illustrative and not restrictive, the scope of the invention being indicated by the claims of the application rather than by the foregoing description, and all changes which come within the meaning and range of equivalency of the claims are therefore intended to be embraced therein.

The invention claimed is:

1. A clamp, comprising:
an upper frame arm;
a lower frame arm assembly having a rear portion and a front portion, wherein the rear portion is hingedly connected to the upper frame arm; and
a clamp assembly including a pivot nut, a knob assembly and a spring member, with the pivot nut pivotally secured to the front portion of the lower frame arm assembly, with the knob assembly having an adjustment screw extending through the upper frame arm and engaging the pivot nut, and with the spring member being positioned about at least a portion of the pivot nut, whereby the upper frame arm and lower frame arm assembly can be locked in a specific location and force can be applied therebetween.

2. The clamp of claim 1 wherein the lower frame arm assembly includes a bottom handle element, and wherein the lower frame arm assembly front portion includes at least one spacer and a fixed end secured to the bottom handle element.

3. The clamp of claim 2 wherein the lower frame arm assembly has a top surface and a bottom surface, wherein the at least one spacer has a top edge and a bottom edge, wherein the fixed end has a top surface, and further wherein the top edge of the at least one spacer engages the bottom surface of the lower frame arm assembly, and the bottom edge of the at least one spacer engages the top surface of the fixed end.

4. The clamp of claim 1 wherein the pivot nut includes a head portion having a head surface and a bottom surface, with a body portion extending from the head surface and a pivot collar extending from the bottom surface.

5. The clamp of claim 4 wherein the body portion has inner and outer walls, wherein the inner walls form an internal chamber, and wherein at least a portion of the inner wall is threaded.

6. The clamp of claim 4 wherein the pivot collar has an opening formed therein, wherein the head portion extends through the front portion of the lower frame arm assembly, and further including a pin extending through the front portion of the lower frame arm assembly and the pivot collar opening.

7. The clamp of claim 4 wherein the upper frame arm has a top surface and a bottom surface, and wherein the spring member is positioned between the pivot nut head portion head surface and the upper frame arm bottom surface.

8. The clamp of claim 1 wherein the upper frame arm has a top surface and a bottom surface, wherein the knob assembly includes a knob in cooperative engagement with the adjustment screw and the top surface of the upper frame arm.

9. The clamp of claim 1 wherein the front portion of the lower frame arm assembly includes a top surface, and further includes one or more spike elements extending from the top surface.

10. The clamp of claim 1 wherein the upper frame arm includes a tip portion, and wherein a pressure monitor assembly is secured to the upper frame arm tip portion.

11. The clamp of claim 10 wherein the upper frame arm tip includes an inner wall defining an opening through the upper frame arm tip, and wherein the pressure monitor assembly includes a clamp stem bushing secured to the inner wall of the upper frame arm tip.

12. The clamp of claim 11 wherein the upper frame arm tip includes a top surface and a bottom surface, and wherein the pressure monitor assembly includes a force indicator element secured to and extending from the top surface of the upper frame arm tip.

13. The clamp of claim 11 wherein the pressure monitor assembly further includes a clamp stem having a base portion and a stem portion, wherein the stem portion is extendable through the upper frame arm tip opening and retained in movable relation therein.

14. The clamp of claim 13 wherein the stem portion of the clamp stem includes an outer wall, with a ridge formed in the outer wall, and further wherein the pressure monitor assembly includes a ring clip member positioned within the ridge, wherein the ring clip member includes a lower surface engageable with the top surface of the upper frame arm tip.

15. A clamp device, comprising:
an upper frame arm having a tip portion, with the tip top portion having an inner wall, a top surface and a bottom surface, with the inner wall defining an opening in the upper frame arm tip;
a lower frame arm;
a clamp stem bushing secured to the inner wall of the upper frame arm tip portion;
a force indicator element secured to and extending from the top surface of the upper frame arm tip portion;
a clamp stem having a base portion and a stem portion, with the stem portion being slidingly engaged with the clamp stem bushing, wherein the clamp stem base portion has a top surface and a bottom surface, and wherein the bottom surface has an opening formed therein so as to form a compartment in the clamp stem base portion; and
a retaining clip secured to the clamp stem.

16. The device of claim 15 wherein the bottom surface has an internal radius, and wherein the compartment has an internal radius, wherein the compartment internal radius is larger than the bottom surface internal radius.

17. The device of claim 15, further including a removable insert maintained within the compartment.

18. The device of claim 15 further including a spring member positioned around the clamp stem and between the top surface of the clamp stem base portion and the bottom surface of the upper frame arm tip portion.

19. The device of claim 18 wherein the clamp stem bushing has a base portion, and wherein the spring member is further positioned around the base portion of the clamp stem bushing.

20. The device of claim 15 wherein the force indicator element is substantially U-shaped with a first arm and a second arm secured to the upper surface of the upper frame arm, and further wherein the force indicator element includes at least one insignia form on at least one of the first and second arms.

21. The device of claim 20 wherein each of the first and second arms includes a front face, a back face, an interior face and an exterior face, and further wherein the insignia form is on the front face, back face, interior face and exterior face of at least one of the first and second arms.

22. The device of claim 20 wherein the insignia form is one of: a marking, a defacement an indentation.

23. The device of claim 15 wherein the clamp stem bushing has a base portion and a trunk portion, wherein the trunk portion is secured to the inner wall of the upper frame arm tip portion.

24. A clamp pressure monitor assembly, comprising:
- a clamp stem bushing having a base portion, a trunk portion and an interior channel;
- a clamp stem having a base portion and a stem portion, wherein the clamp stem base portion has a top surface, a top surface side wall, an intermediate surface and an intermediate side wall, with the stem portion having an outer surface and being insertable into the clamp stem bushing channel so as to be slidingly engaged with the clamp stem bushing, with the stem portion outer surface having a ridge;
- a spring member positioned around the base portion of the clamp stem bushing, wherein the spring member is positioned around the top surface side wall of the clamp stem; and
- a retaining clip positioned within the ridge of the stem portion of the clamp stem.

25. The assembly of claim 24, wherein the clamp stem base portion further includes a top surface and a bottom surface, and wherein the bottom surface has an opening formed therein so as to form a compartment in the clamp stem base portion.

26. The assembly of claim 25, further including a removable insert maintained within the compartment.

27. The assembly of claim 24, further including a force indicator element.

28. A clamp pressure monitor assembly, comprising:
- a clamp stem bushing having a base portion, a trunk portion and an interior channel;
- a clamp stem having a base portion and a stem portion, wherein the clamp stem base portion includes a top surface and a bottom surface, and wherein the bottom surface has an opening formed therein so as to form a compartment in the clamp stem base portion, with the stem portion having an outer surface and being insertable into the clamp stem bushing channel so as to be slidingly engaged with the clamp stem bushing, with the stem portion outer surface having a ridge;
- a spring member positioned around the base portion of the clamp stem bushing; and
- a retaining clip positioned within the ridge of the stem portion of the clamp stem.

* * * * *